United States Patent
Hardy et al.

(10) Patent No.: US 12,194,128 B2
(45) Date of Patent: Jan. 14, 2025

(54) CLEANSING COMPOSITION COMPRISING A NONIONIC AND CATIONIC SURFACTANT MIXTURE AND A CATIONIC ANTIBACTERIAL AGENT

(71) Applicant: Colgate-Palmolive Company, New York, NY (US)

(72) Inventors: Eugene Hardy, Old Bridge, NJ (US); Marian Holerca, Somerset, NJ (US); Rabab Ahmed, Somerset, NJ (US); Evangelia Arvanitidou, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 72 days.

(21) Appl. No.: 17/348,411

(22) Filed: Jun. 15, 2021

(65) Prior Publication Data

US 2021/0308029 A1  Oct. 7, 2021

Related U.S. Application Data

(63) Continuation of application No. 16/993,330, filed on Aug. 14, 2020, now Pat. No. 11,052,031, which is a continuation of application No. 16/448,183, filed on Jun. 21, 2019, now Pat. No. 10,772,817, which is a continuation of application No. 16/032,503, filed on Jul. 11, 2018, now Pat. No. 10,383,808, which is a continuation of application No. 15/049,089, filed on Feb. 21, 2016, now Pat. No. 10,179,100, which is a continuation of application No. 14/690,320, filed on Apr. 17, 2015, now Pat. No. 9,265,714, which is a continuation of application No. PCT/US2013/061801, filed on Sep. 26, 2013.

(51) Int. Cl.
| | | |
|---|---|---|
| *C11D 1/835* | (2006.01) | |
| *A61K 8/41* | (2006.01) | |
| *A61K 8/42* | (2006.01) | |
| *A61K 8/60* | (2006.01) | |
| *A61K 8/86* | (2006.01) | |
| *A61Q 19/10* | (2006.01) | |

(52) U.S. Cl.
CPC ............... *A61K 8/608* (2013.01); *A61K 8/41* (2013.01); *A61K 8/416* (2013.01); *A61K 8/42* (2013.01); *A61K 8/86* (2013.01); *A61Q 19/10* (2013.01); *A61K 2800/30* (2013.01); *A61K 2800/48* (2013.01); *A61K 2800/596* (2013.01)

(58) Field of Classification Search
CPC .. C11D 1/62; C11D 1/75; C11D 1/835; C11D 3/0094; C11D 3/32; C11D 3/48; C11D 7/3263

See application file for complete search history.

(56) References Cited

U.S. PATENT DOCUMENTS

| | | | |
|---|---|---|---|
| 5,290,482 A | 3/1994 | Marschner et al. | |
| 5,326,483 A | 7/1994 | Halloran et al. | |
| 5,641,480 A | 6/1997 | Vermeer | |
| 5,661,170 A | 8/1997 | Chodosh | |
| 5,723,111 A * | 3/1998 | Glover ................... | A61K 8/585 424/70.21 |
| 5,725,887 A | 3/1998 | Martin et al. | |
| 5,827,870 A | 10/1998 | Chodosh | |
| 5,994,383 A | 11/1999 | Dyer et al. | |
| 6,087,400 A | 7/2000 | Dyer et al. | |
| 6,121,224 A | 9/2000 | Fonsny et al. | |
| 6,306,805 B1 | 10/2001 | Bratescu et al. | |
| 6,369,013 B1 * | 4/2002 | Gambogi ............... | C11D 1/835 510/423 |
| 6,488,948 B1 | 12/2002 | Danieli | |
| 6,566,314 B1 | 5/2003 | Murthy et al. | |
| 6,572,846 B2 | 6/2003 | Klein | |
| 6,616,922 B2 | 9/2003 | Taylor et al. | |
| 7,012,048 B2 | 3/2006 | Drovetskaya et al. | |
| 7,112,559 B1 | 9/2006 | Mayhall et al. | |
| 7,169,193 B2 | 1/2007 | Kleen et al. | |
| 7,192,601 B2 | 3/2007 | Walker | |
| 7,754,770 B2 | 7/2010 | Curtis | |
| 8,193,136 B2 | 6/2012 | Taylor et al. | |
| 8,388,991 B2 | 3/2013 | Sondgeroth et al. | |
| 8,795,641 B2 | 8/2014 | Pan | |
| 9,084,734 B2 | 7/2015 | Collier et al. | |
| 9,232,790 B2 | 1/2016 | Moen et al. | |
| 9,265,714 B2 | 2/2016 | Hardy et al. | |
| 10,119,409 B2 | 11/2018 | Charier et al. | |

(Continued)

FOREIGN PATENT DOCUMENTS

| | | |
|---|---|---|
| EP | 1032263 | 9/2000 |
| EP | 1465584 | 10/2004 |

(Continued)

OTHER PUBLICATIONS

Mintel Record # 1245173, Jan. 2010.
Mintel Record # 1268395, Feb. 2010.
Mintel Record # 1371278, Jul. 2010.
Mintel Record # 686467, Apr. 2007.
Mintel Record # 721749, Jun. 2007.
Mintel Record # 766162, Sep. 2007.
Mintel Record # 768340, Sep. 2007.
Mintel Record # 822840, Nov. 2007.
Mintel Record # 928927, Jun. 2008.

*Primary Examiner* — Charles I Boyer

(57) ABSTRACT

An aqueous cleansing composition comprising a cationic surfactant, a nonionic surfactant, and a thickener comprising an alkoxylated methyl glucose ether, wherein a weight ratio of cationic surfactant to nonionic surfactant is greater than 0.9:1. The combination of the cationionic:nonionic surfactant ratio with the alkoxylated methyl glucose ether thickener provides the composition with cold weather stability. Cold weather stability is observed when the composition remains transparent after cold storage.

13 Claims, No Drawings

(56) References Cited

U.S. PATENT DOCUMENTS

| | | |
|---|---|---|
| 10,179,100 B2 | 1/2019 | Hardy et al. |
| 10,383,808 B2 | 8/2019 | Hardy et al. |
| 10,772,817 B2 | 9/2020 | Hardy et al. |
| 2002/0031487 A1* | 3/2002 | Klein .................. A61K 8/40 424/70.28 |
| 2002/0169099 A1* | 11/2002 | Knox .................. A61K 8/39 510/421 |
| 2003/0022941 A1* | 1/2003 | Taylor ................ A01N 33/12 424/70.28 |
| 2004/0071653 A1* | 4/2004 | Bratescu ............ A01N 33/12 424/70.28 |
| 2005/0147575 A1 | 7/2005 | Muller |
| 2005/0189377 A1 | 9/2005 | Lanzendorfer et al. |
| 2005/0198747 A1 | 9/2005 | Emmerling et al. |
| 2007/0077221 A1 | 4/2007 | Seigneurin et al. |
| 2007/0292383 A1 | 12/2007 | Schepky et al. |
| 2008/0275113 A1 | 11/2008 | Huetter et al. |
| 2009/0246163 A1 | 10/2009 | Wahi |
| 2011/0237667 A1 | 9/2011 | Loeffler et al. |
| 2013/0035396 A1* | 2/2013 | Moen .................. A01N 33/12 514/642 |
| 2013/0210923 A1* | 8/2013 | Zhu ..................... A61K 8/39 514/643 |
| 2014/0100288 A1 | 4/2014 | DeSzalay |
| 2014/0170086 A1 | 6/2014 | Pan et al. |
| 2016/0030319 A1* | 2/2016 | Liu ..................... A61Q 19/10 556/134 |
| 2018/0153786 A1* | 6/2018 | De Szalay ......... A61K 8/418 |

FOREIGN PATENT DOCUMENTS

| | | |
|---|---|---|
| WO | 2010/039291 | 4/2010 |
| WO | 2010/127231 | 11/2010 |

\* cited by examiner

CLEANSING COMPOSITION COMPRISING A NONIONIC AND CATIONIC SURFACTANT MIXTURE AND A CATIONIC ANTIBACTERIAL AGENT

CROSS-REFERENCE TO RELATED APPLICATIONS

This application is a continuation of U.S. patent application Ser. No. 16/993,330, filed on Aug. 14, 2020, which is a continuation of U.S. patent application Ser. No. 16/448,183, filed on Jun. 21, 2019, now U.S. Pat. No. 10,772,817, which is a continuation of U.S. patent application Ser. No. 16/032,503, filed on Jul. 11, 2018, now U.S. Pat. No. 10,383,808, which is a continuation of U.S. patent application Ser. No. 15/049,089, filed on Feb. 21, 2016, now U.S. Pat. No. 10,179,100, which is a continuation of U.S. patent application Ser. No. 14/690,320, filed on Apr. 17, 2015, now U.S. Pat. No. 9,265,714, which claims the benefit under 35 U.S.C. § 365 (c) of International Patent Application No. PCT/US2013/061801, filed on Sep. 26, 2013, the entireties of which are incorporated herein by reference.

BACKGROUND

Cationic surfactants can provide antibacterial properties to a cleansing composition. When cationic surfactants are mixed with nonionic surfactants, there is generally a need to use thickeners to increase the viscosity to a level that is expected by consumers for a cleansing composition, such as a liquid hand soap or body wash. While polyacrylate thickeners can increase the viscosity, they can make the cleansing composition opaque or translucent. It would be desirable to provide a cleansing composition containing cationic and nonionic surfactants that is transparent.

BRIEF SUMMARY

An aqueous cleansing composition comprising a cationic surfactant, a nonionic surfactant, and a thickener comprising an alkoxylated methyl glucose ether, wherein a weight ratio of cationic surfactant to nonionic surfactant is greater than 0.9:1.

The combination of the cationionic:nonionic surfactant ratio with the alkoxylated methyl glucose ether thickener provides the composition with cold weather stability. Cold weather stability is observed when the composition remains transparent after cold storage.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

For the purpose of calculating a cationic surfactant to nonionic surfactant ratio, cationic surfactant does not include a cationic antibacterial agent selected from the group consisting of benzalkonium chloride, benzethonium chloride, and mixtures thereof. While these materials may function as a cationic surfactant, they are not included in the calculation.

Transparency is defined as the ability to read 12-point font through the composition contained in a 4 oz clear, glass sample bottle of 4 cm thickness. Transparency is measured after 24 hours at 4.5° C.

Viscosity is measured using a Brookfield RVT viscometer with spindle #5 at 25 rpm at 25° C.

The composition includes a cationic surfactant. The cationic surfactant can be any cationic surfactant, but it excludes the cationic bacterial agent for weight ratio calculation. In certain embodiments, the cationic surfactant comprises a quaternary ammonium alkyl salt. The quaternary ammonium alkyl salt can be an alkyltrimethylammonium salts. The salt can be a halide, such as chloride or bromide, or a methosulfate. The alkyl can be a C8-C24 alkyl or a C14-C18 alkyl. In certain embodiments, the cationic surfactant is cetyltrimethylammonium chloride.

In certain embodiments, the cationic surfactant is present in an amount of 0.1 to 20 weight % of the composition. In other embodiments, the amount is 0.1 to 10, 0.1 to 5, 0.5 to 10, 0.5 to 5, 1 to 5, or 2 to 4 weight %.

The composition includes a nonionic surfactant. The nonionic surfactants can be any nonionic surfactant. Nonionic surfactants include, but are not limited to, amine oxides, fatty acid amides, ethoxylated fatty alcohols, block copolymers of polyethylene glycol and polypropylene glycol, glycerol alkyl esters, alkyl polyglucosides, polyoxyethylene glycol octylphenol ethers, sorbitan alkyl esters, polyoxyethylene glycol sorbitan alkyl esters, and mixtures thereof. Examples of amine oxides include, but are not limited to, laurylamidopropyl dimethylamine oxide, myristylamidopropyl dimethylamine oxide, and mixtures thereof. Examples of fatty acid amides include, but are not limited to, cocomonocthanolamide, lauramide monocthanolamide, cocodiethanolamide, and mixtures thereof.

In certain embodiments, the nonionic surfactant is a combination of an amine oxide and a fatty acid amide. In certain embodiments, the amine oxide is a mixture of laurylamidopropyl dimethylamine oxide and myristylamidopropyl dimethylamine oxide. In certain embodiments, the nonionic surfactant is a combination of lauryl/myristylamidopropyl dimethylamine oxide and cocomonocthanolamide.

In certain embodiments, the nonionic surfactant is present in an amount of 0.1 to 20 weight % of the composition. In other embodiments, the amount is 0.1 to 10, 0.1 to 5, 0.5 to 10, 0.5 to 5, or 0.5 to 3 weight %.

The composition has a cationic:nonionic weight ratio greater than 0.9:1. Optionally, the ratio is at least 1:1.

In certain embodiments, the composition does not contain an anionic surfactant.

The composition also includes a thickener comprising an alkoxylated methyl glucose ether. The alkoxylation can be ethoxylated and/or propoxylated. In certain embodiments, it is ethoxylated. The degree of alkoxylation can be any degree that provides thickening. In certain embodiments, the degree of alkoxylation is 100 to 200. In certain embodiments, the alkoxylation is 120 to 150. The alkoxylated methyl glucose ether can be esterified with fatty acid. In certain embodiments, the alkoxylated methyl glucose ether at least one of an alkoxylated methyl glucose dioleate, an alkoxylated methyl glucose trioleate, alkoxylated methyl glucose distearate. In certain embodiments, the alkoxylated methyl glucoside is at least one of PEG-120 methyl glucose dioleate, PEG-120 methyl glucose trioleate, PEG-120 methyl glucose distearate. In certain embodiments, the alkoxylated methyl glucose ether is PEG-120 methyl glucose dioleate.

The thickener can be present in any amount to provide any desired viscosity level. In certain embodiments, the thickener is present in an amount of 0.1 to 2 weight % of the composition. In other embodiments, the amount is 0.1 to 1, 0.2 to 1, 0.3 to 1, 0.4 to 1, 0.1 to 0.9, 0.1 to 0.8, 0.1 to 0.7, 0.3 to 0.8, or 0.4 to 0.8 weight %. In one embodiment, the amount is 0.4 to 0.7 weight %. In certain embodiments, the viscosity is at least 1000 mPas. In other embodiments, the viscosity is at least 2000, at least 3000, or at least 4000 mPas. In certain embodiments, the viscosity is 1000 to 20000, 3000 to 6000, or 3500 to 5000 mPas.

In certain embodiments, the composition does not include a polyacrylate thickener.

The composition can include a cationic antibacterial agent selected from the group consisting of benzalkonium chloride, benzethonium chloride, and mixtures thereof. In certain embodiments, the composition includes benzalkonium chloride. These cationic antibacterial agents can be included in their regulatory amount, which can be 0.13 weight %.

The composition is aqueous. In certain embodiments, water can be included in an amount of 70 to 95 weight % of the composition. In other embodiments, the amount of water is 90 to 95 weight %.

In certain embodiments, the composition can further include salt, such as sodium chloride to assist in increasing viscosity at upper ranges of viscosity. In certain embodiments, the salt is present at 0.1 to 1.2 weight % of the composition. In certain embodiments, the amount is about 0.6 weight %.

The cleansing compositions can be used to cleanse skin by washing skin with the cleansing composition and optionally rinsing with water.

Examples

The examples and comparative examples are made by mixing of the materials. The compositions are shown in Tables 1 and 2 below. The examples list the cationic:nonionic surfactant ratio. The viscosity and the transparency after storage at 4.5° C. are measured.

TABLE 1

| Material | Example 1 | Example 2 | Example 3 |
|---|---|---|---|
| Deionized Water and minors | QS | QS | QS |
| Lauryl/Myristylamidopropyl dimethylamine oxide | 1.68 | 1.68 | 0.6 |
| Cocomonoethanolamide | 0.92 | 1.02 | 0.4 |
| Cetrimonium chloride | 2.75 | 2.5 | 3 |
| Benzalkonium chloride | 0.13 | 0.13 | 0.13 |
| PEG 120 Methyl Glucose Dioleate | 0.54 | 0.6 | 0.54 |
| Glycerin | 2 | 2 | 2 |
| Sodium chloride | 0.62 | 0.62 | 0.62 |
| Cationic:Nonionic surfactant ratio | 1.06:1 | 0.92:1 | 3:1 |
| Transparency after cold storage | Clear | Clear | Clear |
| Viscosity (mPas) | 4340 | 4740 | 5210 |

TABLE 2

| Material | Comparative A | Comparative B | Comparative C | Comparative D |
|---|---|---|---|---|
| Deionized Water and minors | QS | QS | QS | QS |
| Lauryl/Myristylamidopropyl dimethylamine oxide | 1.68 | 1.51 | 1.68 | 2 |
| Cocomonoethanolamide | 1.1 | 1.12 | 1.12 | 1 |
| Cetrimonium chloride | 2.25 | 2.25 | 2.25 | 1 |
| Benzalkonium chloride | 0.13 | 0.13 | 0.13 | 0.13 |
| PEG 120 Methyl Glucose Dioleate | 0.66 | 0.66 | 0.54 | 0.6 |
| Glycerin | 2 | 2 | 2 | 2 |
| Sodium chloride | 0.62 | 0.62 | 0.62 | 0.62 |
| Cationic:Nonionic surfactant ratio | 0.81:1 | 0.85:1 | 0.80:1 | 0.33:1 |
| Transparency after cold storage | Hazy | Hazy | Hazy | Hazy |
| Viscosity (mPas) | 4600 | 4000 | 4340 | 4470 |

As can be seen in the examples, the combination of the PEG-120 methyl glucose dioleate and the cationic:nonionic surfactant ratio provides a composition that is clear after cold storage and has a desired viscosity over 4000 mPas. When PEG-120 methyl glucose dioleate is present in all compositions, a desired viscosity is obtained, but when the cationic:nonionic surfactant ratio is less than 0.9 in the comparative examples, the composition is hazy after cold storage.

What is claimed is:

1. An aqueous cleansing composition comprising:
A) a cationic antibacterial agent selected from the group consisting of benzalkonium chloride, benzethonium chloride, and mixtures thereof; wherein the cationic antibacterial agent is present in an amount of greater than zero but no more than 0.13 weight % of the composition;

B) a cationic surfactant different from the antibacterial agent;
C) a nonionic surfactant mixture comprising an amine oxide and a fatty acid amide;
D) from 0.54 to 0.6% by weight of a PEG-120 methyl glucose dioleate thickener, wherein:
 i) the weight ratio of the cationic surfactant to the nonionic surfactant is greater than 0.9:1 to keep the composition clear after cold storage; and
 ii) the composition has a viscosity over 4000 mPas.

2. The cleansing composition according to claim 1, wherein the cationic antibacterial agent comprises benzalkonium chloride.

3. The cleaning composition according to claim 1, wherein the thickener further comprises PEG-150 distearate.

4. The cleansing composition according to claim 1, wherein the cationic surfactant comprises a quaternary ammonium alkyl salt.

5. The cleansing composition according to claim 4, wherein the cationic surfactant comprises cetyl trimethyl ammonium chloride.

6. The cleansing composition according to claim 1, wherein the nonionic surfactant comprises lauryl/myristyl amidopropyl dimethylamine oxide and cocomonoethanolamide.

7. The cleansing composition according to claim 1, wherein the thickener is present in an amount of 0.54 or 0.6 weight % of the composition.

8. The cleansing composition according to claim 1, wherein the cationic surfactant is present in an amount of 0.1 to 20 weight % of the composition.

9. The cleansing composition according to claim 1, wherein the nonionic surfactant is present in an amount of 0.1 to 20 weight % of the composition.

10. The cleaning composition according to claim 1, further comprising a salt.

11. The cleansing composition according to claim 1, wherein the composition is substantially free of a polyacrylate.

12. The cleansing composition according to claim 1, wherein the composition is transparent after 24 hours at 4.5° C.

13. A method of cleansing skin comprising applying the cleansing composition according to claim 1, to a skin surface of a subject in need thereof; and optionally rinsing the skin surface with water.

* * * * *